(12) United States Patent
Keränen

(10) Patent No.: US 12,569,343 B2
(45) Date of Patent: Mar. 10, 2026

(54) CATHETER FOR MANIPULATING ANATOMICAL STRUCTURE AND RELATIVE POSITION OF THE CATHETER AND THE ANATOMICAL STRUCTURE

(71) Applicant: HVR CARDIO OY, Espoo (FI)

(72) Inventor: Olli Keränen, Bjärred (SE)

(73) Assignee: HVR CARDIO OY, Espoo (FI)

( * ) Notice: Subject to any disclaimer, the term of this patent is extended or adjusted under 35 U.S.C. 154(b) by 904 days.

(21) Appl. No.: 17/756,152

(22) PCT Filed: Nov. 18, 2020

(86) PCT No.: PCT/FI2020/050775
§ 371 (c)(1),
(2) Date: May 18, 2022

(87) PCT Pub. No.: WO2021/099687
PCT Pub. Date: May 27, 2021

(65) Prior Publication Data
US 2022/0409373 A1 Dec. 29, 2022

(30) Foreign Application Priority Data
Nov. 18, 2019 (FI) ..................................... 20195981

(51) Int. Cl.
*A61F 2/24* (2006.01)
*A61M 25/00* (2006.01)

(52) U.S. Cl.
CPC ....... *A61F 2/2466* (2013.01); *A61M 25/0045* (2013.01)

(58) Field of Classification Search
CPC ...... A61F 2/2442; A61F 2/2448; A61F 2/246; A61F 2/2466; A61M 25/0045;
(Continued)

(56) References Cited

U.S. PATENT DOCUMENTS 4,581,017 A 4/1986 Sahota
5,160,321 A 11/1992 Sahota
(Continued)

FOREIGN PATENT DOCUMENTS

WO 2014128608 A1 8/2014
WO 2014187855 A1 11/2014
WO 2016141195 A1 9/2016

OTHER PUBLICATIONS

Extended European Search Report in EP20891085.1, mailed Oct. 17, 2023, 8 pages.
(Continued)

*Primary Examiner* — William H Matthews
(74) *Attorney, Agent, or Firm* — ArentFox Schiff LLP

(57) ABSTRACT

A catheter for changing or manipulating a shape of a surrounding anatomical structure or position the catheter in relation to said surrounding anatomical structure has distal and proximal ends. Further the catheter includes at least a first body extending along the catheter in the distal end portion of the catheter, wherein said body has an activated state and inactivated state. In said activated state a second diameter or a second volume of the body is bigger than a first diameter or a first volume of the body in said inactivated state. In addition, in said activated state said body is configured to support the catheter to an anatomical structure surrounded the catheter, such as e.g. chordae, blood vessel or urethra, and thereby change a relative position of the catheter and the surrounding anatomical structure and again to change or manipulate the shape of the surrounding anatomical structure or position the catheter in relation to said surrounding anatomical structure.

13 Claims, 4 Drawing Sheets

(58) Field of Classification Search
CPC .......... A61M 25/0105; A61M 25/0155; A61M
2025/2025
See application file for complete search history.

(56) References Cited

U.S. PATENT DOCUMENTS

| | | | |
|---|---|---|---|
| 5,433,706 | A | 7/1995 | Abiuso |
| 6,508,784 | B1 | 1/2003 | Shu |
| 2006/0025750 | A1 | 2/2006 | Starksen et al. |
| 2007/0197858 | A1 | 8/2007 | Goldfarb et al. |
| 2008/0039935 | A1 | 2/2008 | Buch et al. |
| 2009/0069789 | A1 | 3/2009 | Freyman et al. |
| 2010/0198192 | A1 | 8/2010 | Serina et al. |
| 2012/0209375 | A1 | 8/2012 | Madrid et al. |
| 2018/0126127 | A1 | 5/2018 | Devereux et al. |

OTHER PUBLICATIONS

International Search Report and Written Opinion mailed Mar. 26, 2021 issued for PCT Application No. PCT/FI2020/050775.
Search Report mailed Jun. 26, 2020 issued for Finnish Patent Application No. 20195981.

130

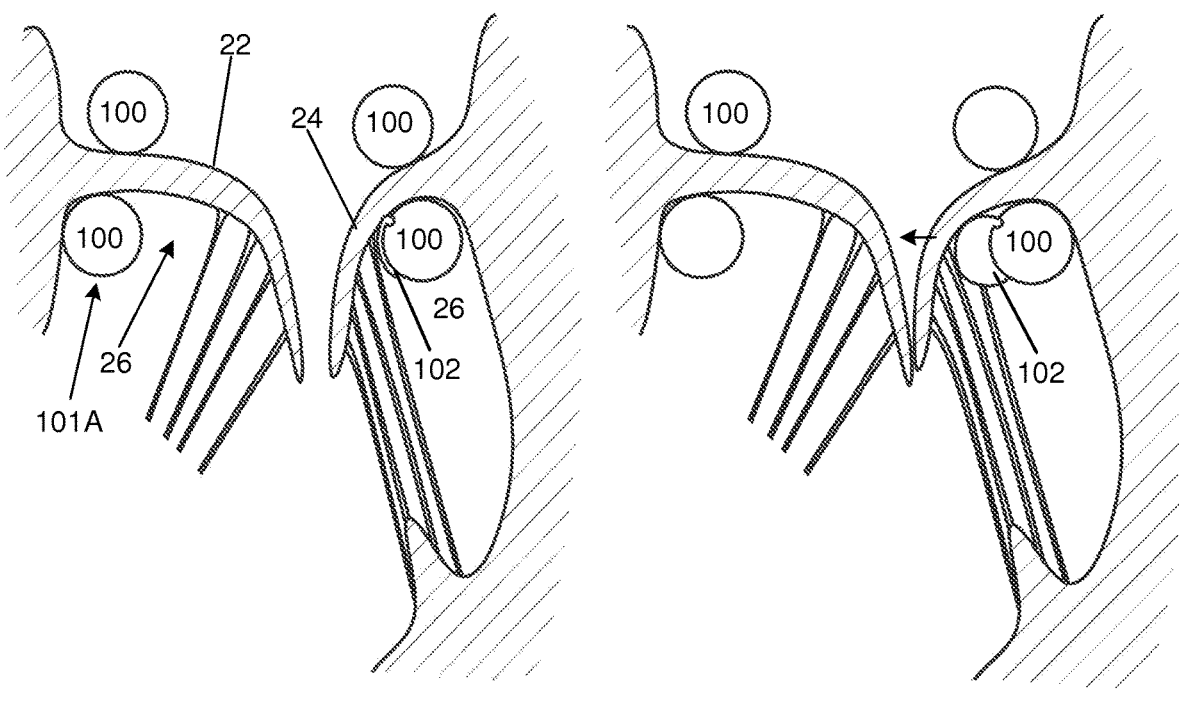
FIG. 3A                          FIG. 3B
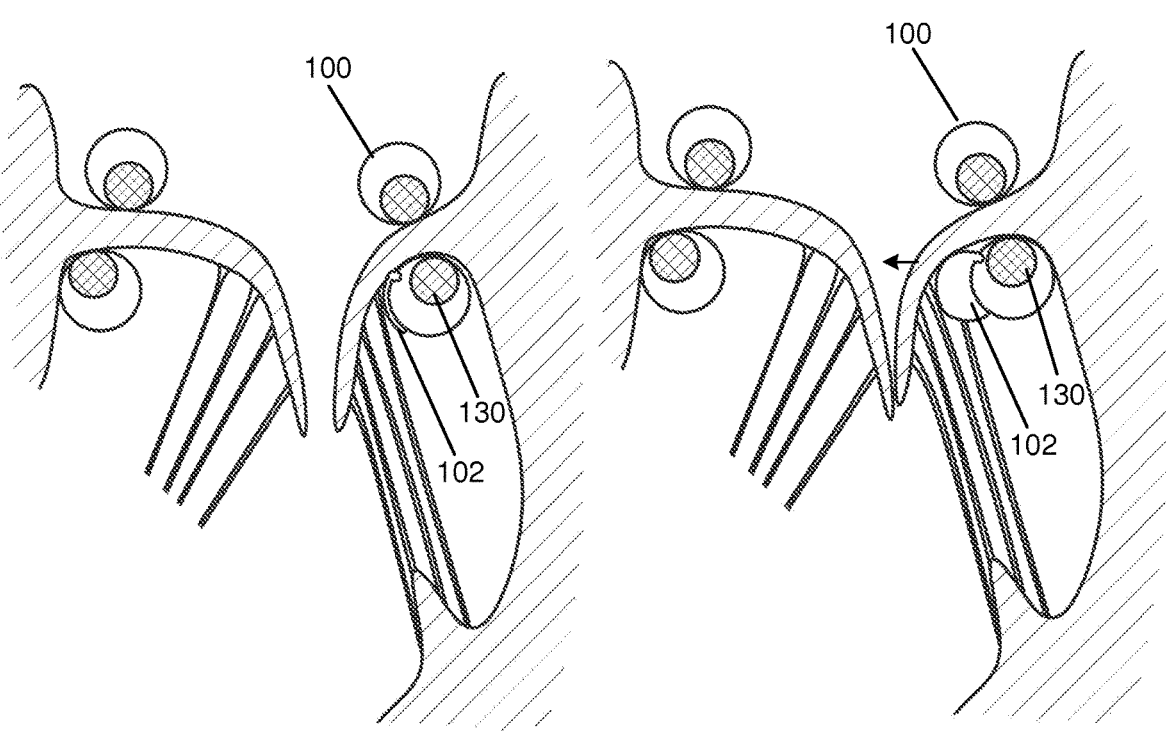
FIG. 3C                          FIG. 3D

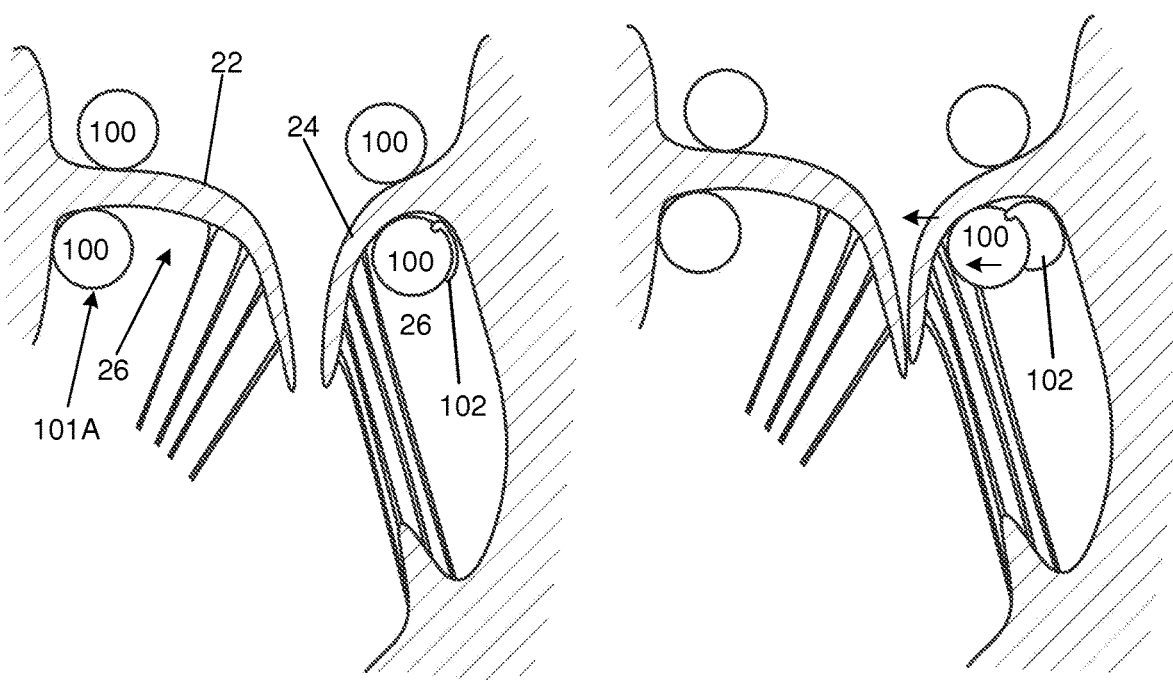
FIG. 4A          FIG. 4B
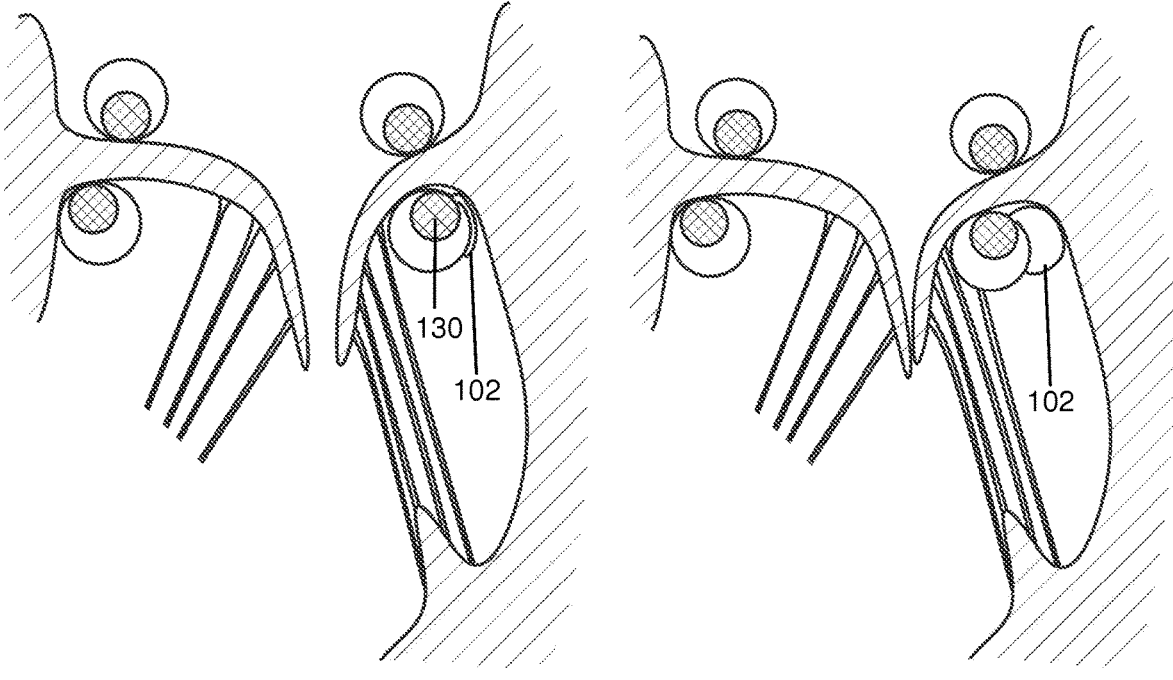
FIG. 4C          FIG. 4D

CATHETER FOR MANIPULATING ANATOMICAL STRUCTURE AND RELATIVE POSITION OF THE CATHETER AND THE ANATOMICAL STRUCTURE

CROSS-REFERENCE TO RELATED APPLICATIONS

This application is a National Phase of PCT Application No. PCT/FI2020/050775, filed on Nov. 18, 2020, which claims priority to Finnish Application No. 20195981, filed on Nov. 18, 2019, the disclosures of which are hereby incorporated by reference in their entireties.

TECHNICAL FIELD OF THE INVENTION

The invention relates to a catheter and in particularly to a catheter for manipulating, such as changing, a shape of a surrounding anatomical structure or positioning the catheter in a desired position or shape in relation to the surrounding anatomical structure. According to an example the invention relates to a catheter for cardiovascular applications manipulating the shape of a left ventricle, such as shape or relative positions of posterior and anterior leaflets or the relative position of the catheter and the anatomical structure, such as the left ventricle or posterior and anterior leaflets or an annulus. The catheter according to the invention can be used also for manipulating other anatomical structures or positioning the catheter in relation to other anatomical structures, such as a urethra, esophagus, blood vessel, bile ducts, intestine, and in particularly for enlarging or otherwise manipulating stricture or stenosis in these anatomical structures, for example.

BACKGROUND OF THE INVENTION

Few applications are known for manipulating a shape of a surrounding anatomical structure, such as changing the shape of a portion of the heart, like downsizing and reshaping of the valve annulus. For example, diseased mitral valves frequently need repair to function properly. The mitral valve leaflets or supporting chordae may degenerate and weaken or the annulus may dilate leading to valve leak (valve insufficiency).

FIG. 1A illustrates a portion of the heart 12, the mitral valve 18, and the left ventricle 14. The mitral valve is at its boundary circumferenced by an annulus 20. The valve has two cusps or leaflets 22, 24. Each of these cusps or leaflets 22, 24 are connected to a respective papillary muscle 27, 29 via their respective connecting chordae 26, 28. In normal healthy individuals the free edges of the opposing leaflets will close the valve by coaptation. However, for some individuals the closure is not complete, which results in a regurgitation, also called valvular insufficiency, i.e. back flow of blood to the left atrium making the heart less effective and with potentially severe consequences for the patient. FIG. 1B illustrates a mitral valve 18, in which the leaflets 22, 24 do not close properly. This commonly occurs when the annulus 20 becomes dilated.

One surgical procedure to correct this is to remove a portion of the leaflet 24 and stitch the cut edges together with one another. The procedure will pull back the annulus 20 to a more normal position. However, the strength of the leaflet 24 is altered. Another way is to push the posterior and anterior leaflets against each other, such as downsizing and reshaping of the valve annulus so that the closure of the leaflets is again complete.

For example, a system is known [WO2014187855A1] where a removable and flexible elongate downsizing device is inserted temporary into a coronary sinus adjacent a mitral valve, where the device has a distal anchoring portion to anchor the distal end of the device into the surrounding anatomical structure. The distal anchoring portion is movable in relation to a proximal portion of the device, whereupon after anchoring the distal end the distal anchoring portion is pulled towards the proximal portion, whereby the distance between the two portions is reduced to a shorter distance to provide the downsizing.

In order to maintain the downsized shape where the closure is completed, an implant is typically fixed for example to the annulus to that the changed shape will remain also when the downsizing device is removed. One prior art cardiac implant 110, or annuloplasty ring, is depicted in FIG. 2. The implant may comprise one or more loop-shaped structures 111, 112. Typically one first loop-shaped structure is configured to abut a first side of the heart valve and one second loop-shaped structure is configured to abut a second, opposite, side of the valve to thereby trap a portion of the valve tissue 20 between the second and the first support structures 111, 112.

Even if the known solutions are good for their dedicated purposes, there are still some disadvantages, especially when there is also needs to insert the implant at the same for example to maintain the changes in the shape of the anatomical structure. The changes for the shape of the anatomical structure is done by the first catheter delivery system and simultaneously the implant in delivered via a second catheter, whereupon there are at least two different catheters introduced to the body at the same time and via different routes. This makes the operation complex for an operator and at the same dramatic to organs of a patient due the insertion of number of catheters.

SUMMARY OF THE INVENTION

An object of the invention is to alleviate and eliminate the problems relating the known prior art. Especially an object of the invention is to provide a catheter, by which a shape of an anatomical structure or by which the relative position of the catheter and the anatomical structure can be manipulated or changed in a controllable manner to a favourable form or position. In addition, an object of the invention is also to introduce an object, such as an implant or other medium, next to the anatomical structure when the shape of an anatomical structure is manipulated to the favourable form, and without any further catheters. Further object is to position the catheter so that the object, such as an implant, can be introduced into a desired position in said anatomical structure accurately by the catheter.

The object of the invention can be achieved by the features of independent claims.

The invention relates to a catheter according to claim 1.

According to an embodiment of the invention a catheter for changing or modification a shape of a surrounding anatomical structure or positioning the catheter in relation to the anatomical structure comprises posterior and distal ends. In addition, the catheter comprises also at least a first body in the distal end portion of the catheter, wherein said body comprises an activated state and inactivated state. In the activated state the diameter ($d_2$) or volume ($V_2$) of the body is bigger than the diameter ($d_1$) or volume ($V_1$) of the body in said inactivated state. Advantageously the catheter is a steerable catheter, whereupon in particularly the distal can be turned into an appropriate position so that the body, when activated, is able to manipulate the surrounding anatomical structure or e.g. change or move the position of the catheter, especially the distal end, in relation to said surrounding anatomical structure so that e.g. an implant can be fed in a desired position in relation to the surrounding anatomical structure.

In said activated state the body is configured to support the catheter to an anatomical structure surrounded the catheter, such as e.g. chordae, blood vessel or urethra, for example, and thereby change a relative position of the catheter and the surrounding anatomical structure and again to change or modify the shape of the surrounding anatomical structure or position the catheter in relation to the surrounding anatomical structure.

According to an advantageous embodiment the catheter can be introduced next to an annulus of a mitral valve, and in particularly in a left ventricle and in more advantageously between chordae and a posterior left ventricle wall, most advantageously into a sub-annular groove. According to an embodiment the body arranged in the anterior portion of the catheter (inside curve of the catheter so to the direction where the distal end of the catheter turns naturally tends to turn) can be configured to be supported against the chordae and/or posterior leaflet, whereupon the body is configured to move or push a posterior annulus leaflet towards an anterior leaflet due to straightening the curve of the catheter in the portion where the body extends along the catheter, when the state of the body is changed from inactivated state to said activated state.

According to another embodiment the catheter may have the body arranged in the posterior portion of the catheter, whereupon the body is configured to be supported against the left ventricle wall. In this embodiment the body arranged in the posterior portion of the catheter is configured to move or push the catheter towards the posterior annulus leaflet and thereby move the posterior annulus leaflet towards the anterior leaflet, when the state of the body is changed from inactivated state to said activated state.

As discussed earlier, the catheter may also be used in connection with other anatomical structures, such as with tubular anatomical structures. Few examples are a urethra, esophagus, blood vessel, bile ducts, intestine. Here the catheter with the body can be used to perform one-sided enlargement and thereby manipulate for example stricture or stenosis in said tubular anatomical structure, when the state of the body is changed from inactivated state to said activated state.

The body (one or more) is advantageously arranged to extend along the catheter in the longitudinal direction of the catheter either in the posterior (outside curve) or anterior (inside curve) portion of the catheter, depending on the application. According to an embodiment the catheter advantageously comprises a lumen for delivering a medium, such as liquid, to the body of the catheter and thereby chancing the body from the inactivated state to the activated state. The lumen (advantageously the same lumen as used for activating, but the invention is not limited whether there is another lumen) for delivering the medium, such as liquid, from the body back and thereby chancing the body from the activated state to the inactivated state.

In addition, according to an embodiment the catheter may also comprise an introduction lumen for introducing an implant or other object from the proximal end to the distal end and again next to the anatomical structure. The object may be for example an annuloplasty ring.

Still according to an embodiment, the body of the catheter may be permeable, whereupon the catheter with the permeable body can be used to permeate a medium, such as medicament, drug or contrast agent, delivered to the body to the surrounding anatomical structure. In one embodiment there can be an additional permeable layer on the surface of the body having own lumen for delivering the medium. Advantageously the own lumen is separate from the lumen used for activating and deactivating the body.

Further, according to an embodiment, the catheter may also comprise a radiopaque member advantageously in the distal end, and in particularly at least one end portion of the body, or even in the both ends of the body, whereupon it is easier to position the body into an appropriate position next to the surrounding anatomical structure.

The embodiments described in this document offer many advantages over the known prior art, such as possibility to change or manipulate a shape of an anatomical structure in a controllable manner to a favourable form or position the catheter in relation to the anatomical structure. In addition, also an object, such as an implant or other medium, can be introduced at the same catheter next to the anatomical structure when the shape of an anatomical structure is manipulated to the favourable form, such as downsized annulus, and without any further catheters. In addition, the catheter can be positioned so that the object, such as an implant, can be introduced into a desired position in relation said anatomical structure accurately.

In particularly, the catheter with the one or more body can be used to support the surrounding weakened tissue structure temporarily while at the same time allow to repair the area, such as introducing and fixing an annuloplasty ring to keep the reshaped shape of the tissue. In addition, the catheter with the one or more body can be used to reshape temporarily twisted or ruptured structure.

The exemplary embodiments presented in this text are not to be interpreted to pose limitations to the applicability of the appended claims. The verb "to comprise" is used in this text as an open limitation that does not exclude the existence of also unrecited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objects and advantages thereof, will be best understood from the following description of specific example embodiments when read in connection with the accompanying drawings.

BRIEF DESCRIPTION OF THE DRAWINGS

Next the invention will be described in greater detail with reference to exemplary embodiments in accordance with the accompanying drawings, in which:

FIGS. 3A-4D illustrate examples of catheters according to advantageous embodiments of the invention.

DETAILED DESCRIPTION

Figure 1A:
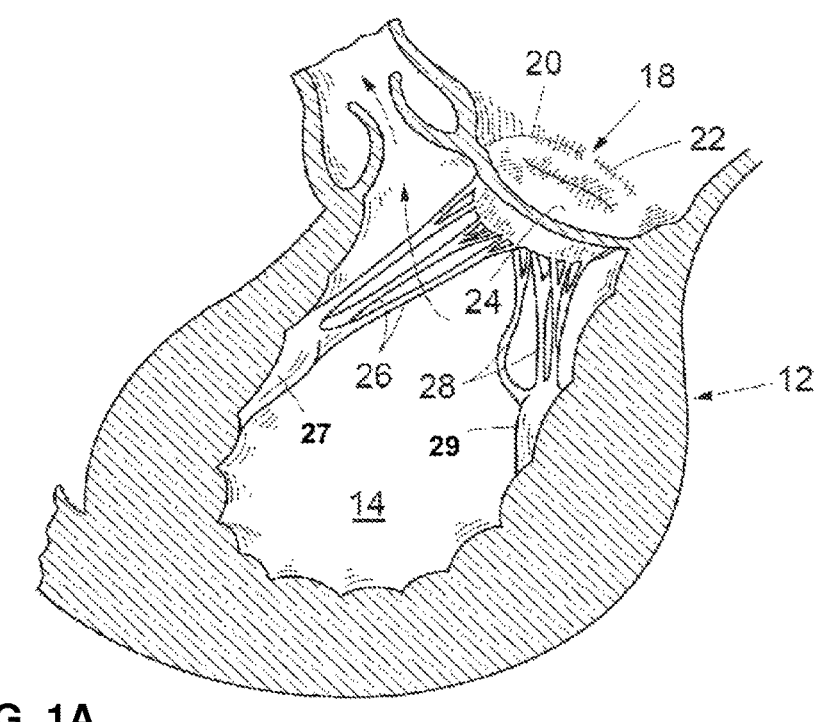
FIGS. 1A-1B illustrate schematically a portion of a heart and mitral valve.
Figure 1B:
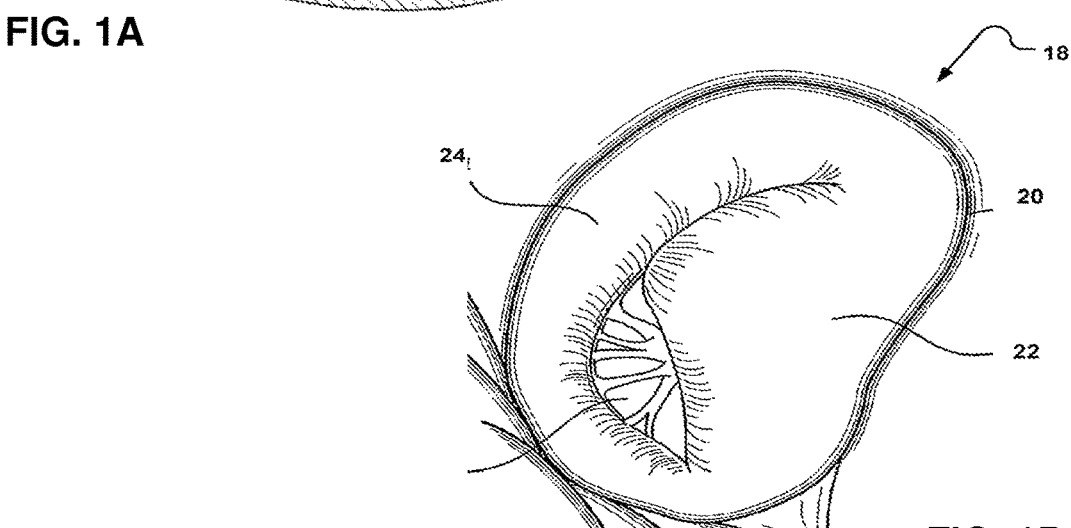

FIGS. 1A-1B illustrating schematically a portion of a heart and mitral valve are already discloses in the connection with the background portion of the invention.

Figure 2:
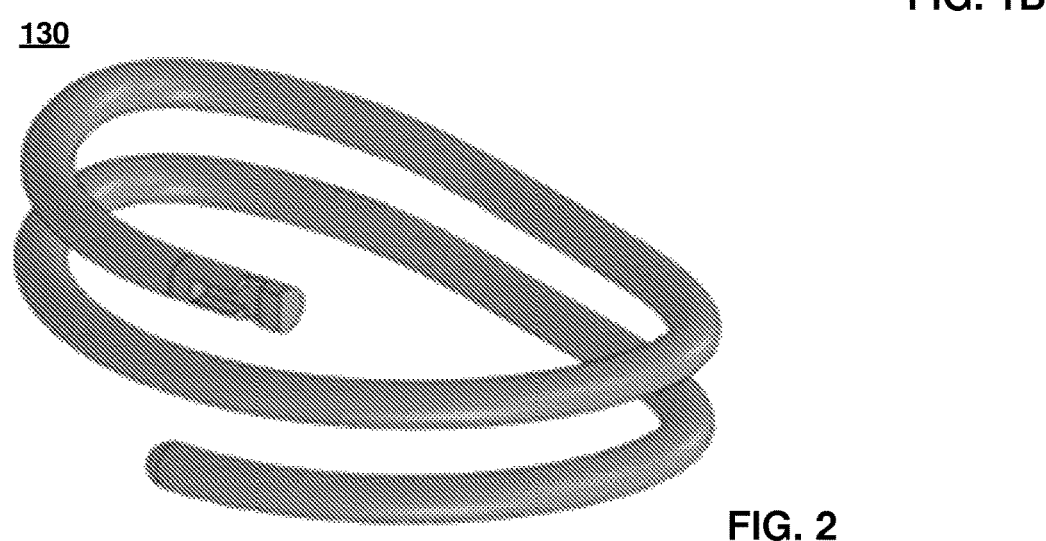
FIG. 2 illustrates an exemplary annuloplasty ring used for treating a defective mitral valve.

FIG. 2 illustrating an exemplary annuloplasty ring used for treating a defective mitral valve is already discloses in the connection with the background portion of the invention.

In FIG. 3A the leaflets 22, 24 does not close properly the valve by coaptation due to degeneration and weakening of the mitral valve leaflets or supporting chordae, for example. In addition, the distal portion 101A of the catheter 100 is introduced between the chordae and a posterior left ventricle wall, more particularly into a sub-annular groove 26. The catheter comprises at least a first body 102, in the distal end portion 101A of the catheter. The body comprises an inactivated state (FIGS. 3A, 3C) and activated state (FIGS. 3B, 3D), wherein in said activated state the diameter ($d_2$) or volume ($V_2$) of the body is bigger than the diameter ($d_1$) or volume ($V_1$) of the body in said inactivated state. FIG. 3A illustrate the introduced catheter in the inactivated state, whereas in FIG. 3B the catheter is in the activated state.

In FIGS. 3A-3D the body 102 is arranged into the anterior side (inside curve) of the catheter. In this embodiment, the distal end 101A of the catheter (more particularly the outer curve portion of the distal end of the catheter when the catheter takes its natural curved shape) is advantageously supported the anatomical structure, such as posterior left ventricle wall. Now, when the diameter or the volume of the body 102 is changed from the inactivated state to the activated state, the distal end 102 of the catheter tends to straighten, but because it is supported to the anatomical structure, the increasing volume and/or diameter of the body 102 forces the distal end portion 101C of the catheter straighten, whereupon the posterior portion (outside of the curve) is forced towards anterior portion (inside curve) in the direction of the arrow 103 (see FIGS. 5A, 5B, where in FIG. 5A the body is in the inactivated state and in FIG. 5B the body is in the activated state). In this way e.g. the posterior leaflet 24 in this example can be moved towards the anterior leaflet 22, as is the case in FIGS. 3B, 3D. In analogous way in other applications some other anatomical structure can be moved or the position of the catheter can be moved in relation to the surrounding anatomical structure.

In FIGS. 4A-4D the body 102 is arranged into the posterior side of the catheter, and in this embodiment there is no need to support the distal end 101A of the catheter to the anatomical structure, like posterior left ventricle wall. Now, when the diameter or the volume of the body 102 is changed from the inactivated state to the activated state, the enlarging body 102 will be supported into the wall and push the catheter (inside curve) towards the posterior leaflet 24 and thereby push the posterior leaflet 24 towards the anterior leaflet 22 and thus allowing complete closure of the leaflets again in this example. However, it is to be noted that in analogous way in other applications some other anatomical structure can be moved or the position of the catheter can be moved in relation to the surrounding anatomical structure.

In both examples illustrated in FIGS. 3A-3D and 4A-4D the catheter may be used also for introducing implant 130 or other medium, such as medicine or contrast agent, to the anatomical structure in question. According to an embodiment the wall of the body 102 may be permeable whereupon medical medium can be introduced to the anatomical structure be feeding via a lumen of the catheter to the body 102 and again due to the permeable wall of the body 102 again to a final destination.

Figures 5A, 5B, 5C, 6A, 6B, 6C:
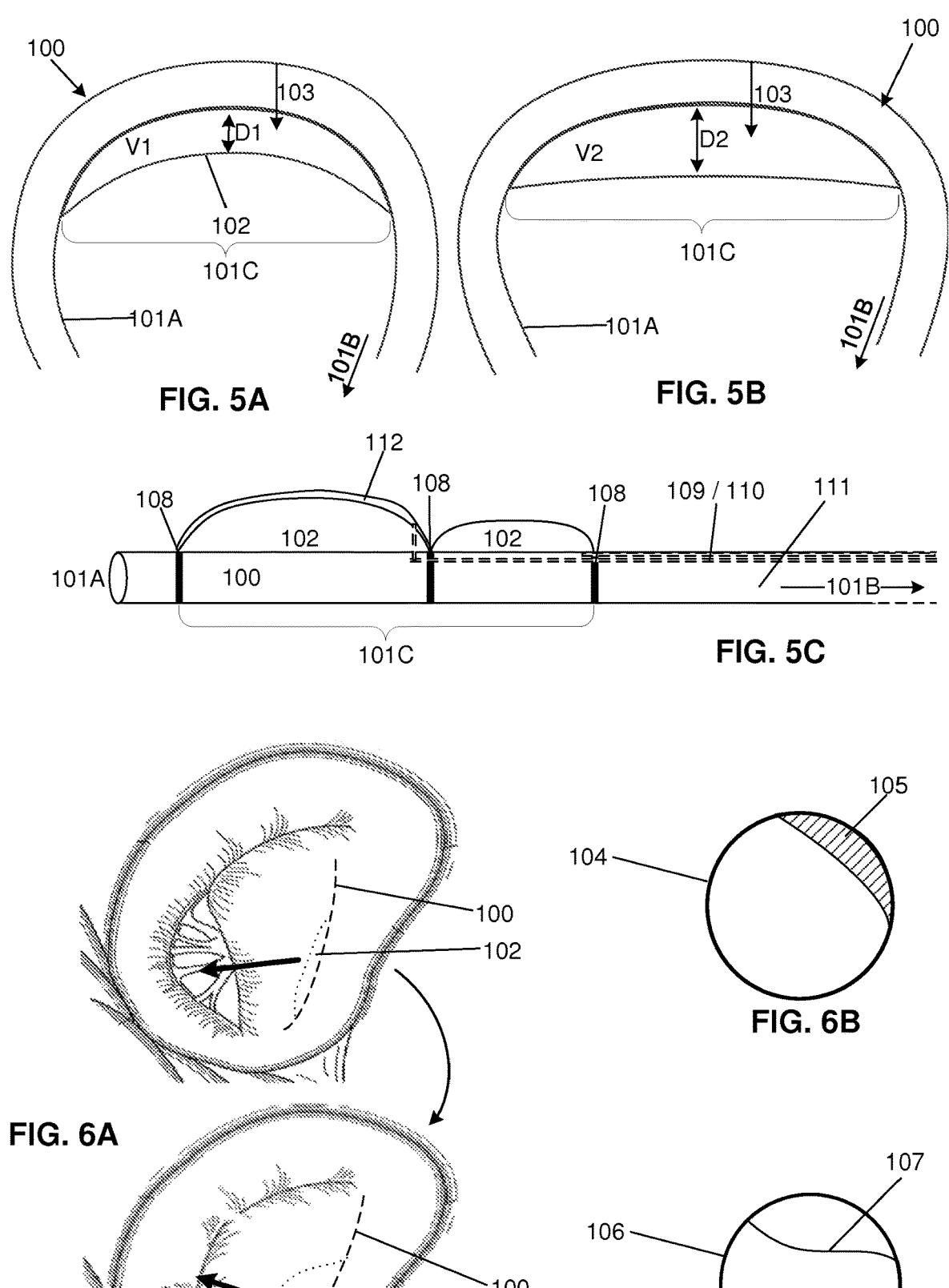
FIGS. 5A-5C illustrate example side views of a catheter according to advantageous embodiment of the invention.
FIGS. 6A-6C illustrate additional examples of anatomical structures where the catheter of the invention can be used for manipulating the anatomical structures according to advantageous embodiment of the invention.

FIG. 5C illustrates an exemplary catheter 100 having distal 101A and proximal 101B ends. The two bodies 102 are advantageously extending along the catheter according to the invention. In FIG. 5C both bodies 102 are activated, but as can be seen the first body 102 (left side) is activated bigger that the second one 102 (right side). In addition, the exemplary catheter has also radiopaque members 108 at the end portions of the bodies 102 for helping position the catheter and in particularly the bodies into appropriate positions. Further, the catheter may also comprise a radiopaque member at the distal end 101A (not shown). Still in addition, the catheter advantageously comprises own lumen 109 for each body 102 in order to activate or inactive the each body 102 separately and independently. The activation may be implemented e.g. by feeding a medium, such as salted solution, and the inactivation by sucking up the medium back from the body 102.

Furthermore, the wall of the body 102 may be permeable, whereupon e.g. liquid medicament can be fed via the lumen 110 to the (chosen) body and thereby to the anatomical structure, for example when the structure is manipulated by the activated body 102.

More advantageously the body 102 of the catheter comprises permeable layer 112 on the surface of the body 102, wherein the surface layer 112 is connected to a delivery lumen 110 separate from the lumens used for activating and inactivating the bodies 102. The permeable surface layer is configured to permeate a medium delivered to the permeable surface layer 112 to the surrounding anatomical structure.

Further, the catheter comprises additionally an introduction lumen 111 for introducing an implant 130 or other object from the proximal end 101B to the distal end 101A and again next to the anatomical structure.

FIGS. 6A-6C illustrate additional examples of anatomical structures where the catheter 100 of the invention can be used for manipulating the anatomical structures according to advantageous embodiment of the invention. FIG. 6A illustrates a mitral valve, where the anterior (dominant) leaflet 22 does not function properly because the annulus in P1 and/or P2 area is expanded and does not provide complete closure, as can be seen in the upper FIG. 6A (it closes only one-sided). The dysfunction of the mitral valve shown in the upper FIG. 6A can be fixed by the catheter 100 provided with at least one body 102 according to the invention, namely when the catheter and in particularly the body or bodies 102 are positioned in an appropriate way, and most advantageously into the sub-annular groove (as is the case in FIGS. 3A-3D, for example). Then the activating an appropriate body 102 of the catheter, advantageously situated in the next of the expanded area, can move or push the expanded area of the annulus (in practice leaflet) towards center area of the annulus (changing or manipulating the anatomical structure) and thereby providing complete close, as is the case in the lower FIG. 6A.

In addition to the manipulating the mitral valve annulus or position the catheter, the catheter of the invention can be used also for introducing an implant, such as an annuloplasty ring in the next of the annulus (into the upper and/or lower side, or into the atrial and/or ventricular side of the annulus). This is advantageously done after the shape or form of the annulus has already reshaped (one can say, downsized) and/or after the catheter is positioned in relation to the anatomical structure, as described elsewhere in this document. When the implant is introduced, it is advantageously fixed to the annulus area to keep the reshaped form of the annulus, after which the body 102 can be changed to the inactivated state and the catheter 100 can be removed.

The anatomical structure may even have more than one asymmetry points, whereupon the catheter having more than one bodies 102 can be used. For example, the first body 102 may be oriented with the first asymmetry point and change the volume or diameter of said first body to a first increased dimension required by the first asymmetry point, and then the second body with the second asymmetry point and change the volume or diameter of said second body to a second increased dimension required by the second asymmetry point. The first and second increased dimensions of the bodies may be different, thereby causing different manipulating forces to different portions of the anatomical structures faced with the different bodies of the catheter according to the invention. Also, the positions of the different portions of the catheter can be positioned in relation to the anatomical structure at least partly independently in this way.

FIG. 6B illustrates on example of a tubular anatomical structure, such as esophagus 104 or the like, where there is a one-sided stenosis 105. Now the distal end 101A of the catheter 100 can be introduced via the tubular anatomical structure, and then turn the distal end 101A (due to steerability) into an appropriate angle, before activating the body 102 (one or more bodied) of the catheter. The activated body is at first advantageously oriented in such a way that it will for example push the stenosis 105 and can at the same time also introduce medicaments, if appropriate. Again, if there are more than one stenosis, more than one bodies can be activated.

Further, FIG. 6C illustrate another example of a tubular anatomical structure, such as urethra 106 or the like, where there is for instance a one-sided stricture 107, as is the case in FIG. 6C. Now the distal end 101A of the catheter 100 can be introduced via the tubular anatomical structure, and then turn the distal end 101A (due to steerability) into an appropriate angle, before activating the body 102 (one or more bodied) of the catheter. When at least one of the bodies 102 of the catheter is turned into an appropriate position and activated, the stricture can be manipulated by due to the activation of the body, such as destroying or breaking the structure of the stricture or stenosis. In addition, according to an embodiment, if at least one body 102 is permeable to a certain medicament, also medicament can be introduced via a lumen (not shown in Figures) to the body and again through the wall of the body to the anatomical target, such as to the stricture or stenosis.

The invention has been explained above with reference to the aforementioned embodiments, and several advantages of the invention have been demonstrated. It is clear that the invention is not only restricted to these embodiments, but comprises all possible embodiments within the spirit and scope of the inventive thought and the following patent claims.

The features recited in dependent claims are mutually freely combinable unless otherwise explicitly stated.

The invention claimed is:

1. A catheter for changing a shape of an anatomical structure in a vicinity of the catheter or for positioning the catheter in relation to the anatomical structure, the catheter having distal and proximal ends, wherein the catheter comprises:

a body in a distal end portion of the catheter, wherein said body comprises an activated state and an inactivated state, wherein in said activated state a second diameter or a second volume of the body is bigger than a first diameter or a first volume of the body in said inactivated state, and wherein in said activated state said body is configured to push the catheter toward the anatomical structure in the vicinity of the catheter and thereby change a relative position between the catheter and the anatomical structure in the vicinity of the catheter, to change or manipulate the shape of the anatomical structure in the vicinity of the catheter, or to position the catheter in relation to said anatomical structure in the vicinity of the catheter.

2. The catheter of claim 1, wherein the body is arranged to extend along the catheter in a longitudinal direction of the catheter and in a posterior or anterior portion of the catheter.

3. The catheter of claim 1, wherein the catheter comprises a lumen for delivering a medium to said body and thereby changing the body from the inactivated state to the activated state.

4. The catheter of claim 1, wherein the catheter comprises a lumen for delivering a medium from said body and thereby changing the body from the activated state to the inactivated state.

5. The catheter of claim 1, wherein the catheter comprises additionally an introduction lumen for introducing an implant or object from the proximal end to the distal end and next to the anatomical structure.

6. The catheter of claim 1, wherein the body of the catheter is permeable and is configured to permeate a medium delivered to the body to the anatomical structure in the vicinity of the catheter.

7. The catheter of claim 6, wherein the body of the catheter comprises permeable layer on a surface of the body, wherein the permeable surface layer is connected to a delivery lumen and is configured to permeate a medium delivered to the permeable surface layer to the anatomical structure in the vicinity of the catheter.

8. The catheter of claim 1, wherein the catheter is a steerable catheter.

9. The catheter of claim 1, wherein the catheter is configured to be introduced next to an annulus of a mitral valve in a left ventricle or between chordae and a posterior left ventricle wall, or into a sub-annular groove.

10. The catheter of claim 9, wherein a body arranged in an anterior portion is configured to be supported against the chordae or a posterior leaflet and a body arranged in a posterior portion is configured to be supported against the left ventricle wall, whereupon:

the body arranged in the anterior portion is configured to move a posterior annulus leaflet towards an anterior leaflet of the mitral valve due to straightening a curve of the catheter in the portion where the body extends along the catheter, and the body arranged in the posterior portion is configured to move the catheter towards a posterior annulus leaflet of the mitral valve and thereby move the posterior annulus leaflet of the mitral valve towards the anterior leaflet of the mitral valve when the state of the body is changed from said inactivated state to said activated state.

11. The catheter of claim 1, wherein the catheter is configured to be introduced into a tubular anatomical structure and whereupon the body is arranged to perform one-sided enlargement and thereby manipulate stricture or stenosis in said tubular anatomical structure, when the state of the body is changed from said inactivated state to said activated state.

12. The catheter of claim 1, wherein the catheter comprises a radiopaque member at a distal end of the catheter, a radiopaque member at one end portion of the body, or radiopaque members at both portions of the body.

13. A manipulating method for changing or manipulating a shape of an anatomical structure in the vicinity of a catheter or for positioning the catheter in relation to said anatomical structure in the vicinity of the catheter, wherein the catheter comprises distal and proximal ends, and wherein the catheter further comprises:

at least a body in a distal end portion of the catheter, wherein said body comprises an activated state and an inactivated state, wherein in said activated state a second diameter or a second volume of the body is bigger than a first diameter or a first volume of the body in said inactivated state, and wherein in said activated state said body pushes the catheter toward an anatomical structure in the vicinity of the catheter and thereby change a relative position between the catheter and the anatomical structure or to change or manipulate the shape of the anatomical structure or position the catheter in relation to said anatomical structure.

\* \* \* \* \*